United States Patent
Kuo et al.

(10) Patent No.: US 7,093,501 B2
(45) Date of Patent: Aug. 22, 2006

(54) PROCESS AND DEVICE FOR MEASURING FLOW PARAMETERS

(75) Inventors: Artur Chung-Che Kuo, Lübeck (DE); Stefan Zimmermann, Lübeck (DE)

(73) Assignee: Drägerwerk, Aktiengesellschaft (DE)

( * ) Notice: Subject to any disclaimer, the term of this patent is extended or adjusted under 35 U.S.C. 154(b) by 0 days.

(21) Appl. No.: 11/259,656

(22) Filed: Oct. 26, 2005

(65) Prior Publication Data

US 2006/0107755 A1    May 25, 2006

(30) Foreign Application Priority Data

Nov. 19, 2004   (DE)   ................ 10 2004 055 968

(51) Int. Cl.
  *G01F 1/32* (2006.01)
(52) U.S. Cl. ................... 73/861.23; 73/861
(58) Field of Classification Search ............ 73/861.23, 73/861.21, 861.42, 861.52, 861
See application file for complete search history.

(56) References Cited

U.S. PATENT DOCUMENTS 5,287,851 A * 2/1994 Beran et al. ........... 128/204.23
6,354,147 B1 * 3/2002 Gysling et al. ............ 73/61.79
6,691,584 B1 * 2/2004 Gysling et al. .......... 73/861.42

FOREIGN PATENT DOCUMENTS

| DE | 101 04 462 A1 | 8/2002 |
| DE | 103 52 652 A1 | 6/2005 |
| EP | 0 444 243 A2 | 9/1991 |

* cited by examiner

*Primary Examiner*—Harshad Patel
(74) *Attorney, Agent, or Firm*—McGlew & Tuttle, PC (57) ABSTRACT

A process device and system for measuring flow parameters in flowing gases is provided in which a device for flow-induced sound generation is in the area of the flow to be measured. A measurement of the frequency and/or the level of the sounds generated is made during the flow to be measured as acoustic parameters. A determination is made as to the flow parameters to be measured by processing the measured acoustic parameters. The process makes possible, in particular, the measurement of the volume flows during respiration near the patient.

21 Claims, 6 Drawing Sheets

PROCESS AND DEVICE FOR MEASURING FLOW PARAMETERS

CROSS REFERENCE TO RELATED APPLICATIONS

This application claims the benefit of priority under 35 U.S.C. § 119 of German Application DE 10 2004 055 968.6 filed Nov. 19, 2004, the entire contents of which are incorporated herein by reference.

FIELD OF THE INVENTION

The present invention pertains to a process and a device for measuring flow parameters in flowing gases. It can be used wherever volume and mass flows are to be determined in flowing gases.

BACKGROUND OF THE INVENTION

To determine volume and mass flows in flowing gases, it is usual and meaningful to determine flow parameters at individual measuring points and to determine the overall flow from these measured values by extrapolation over time and/or space. Flow parameters are either measured for this purpose directly or derived from the measurement of other physical variables, which unambiguously depend on the flow parameters, by the use of various evaluation algorithms. The measurement method is selected, as a rule, depending on a great variety of requirements and boundary conditions. These include the space available, the necessary accuracy, the costs associated with the measurement, the presence of supply media, various requirements on handling and comfort and the applicability of suitable measuring means.

The fields of applications in which the boundary conditions must be taken into consideration include various flow measurements in connection with the performance of the artificial respiration of patients. The present invention will therefore be explained below largely in respect to medical applications, without wishing to explicitly limit the present application to this field of application.

To make it possible to obtain reliable information on the respiration status of a patient from flow measurements, distortions due to a possible elastic deformation of the pipeline system for guiding the gas must be avoided. Measuring points located as close to the patient as possible are therefore usually desirable. Furthermore, the measuring set-up is to be designed such that the flow resistance will be low in order to keep the load on the patient as low as possible. Design-related increases in the dead space are to be avoided especially in case the respiratory system is compromised or in case of small tidal volumes. Due to use near the patient in the field of clinical medicine, there must be, moreover, insensitivity to particles being carried within the gas flow and to sputum. Since flow balances are frequently to be established from the flow measurements, reliable information on the direction of flow is, moreover, usually desirable.

It is known that flow measurements can be carried out in the respiration system by the use of so-called hot wire anemometers (DE 10104462 A1). Hot wire anemometers are usually accommodated for this purpose in separate components, which ensure that the flow to be measured will become uniform, and possibly near the patient, i.e., usually between the Y-piece and the tube or directly at or after the Y-piece. Due to accommodation in a separate component, the dead space will become larger or arrangement at a relatively great distance from the patient will become necessary.

Another drawback of this process is its sensitivity to particles being carried in gas flows as well as contamination by sputum. Since it is an electric measurement method, supply lines to the measuring element proper are, moreover, always necessary, which may lead to disadvantages in clinical practice in terms of applicability and user friendliness.

DE 103 52 652.8 relates to carrying out flow measurements in respiration systems by ultrasound measurements. A defined measuring section, which is investigated with ultrasound, is usually preset for this by a separate component. By evaluating the received ultrasound, it is possible to obtain information on the velocity of flow and the direction of flow. One drawback of this process is likewise the usually inevitable enlargement of the dead space as well as the complicated electronic evaluating and supply system, which must be connected directly to the measuring element in this case as well.

SUMMARY OF THE INVENTION

The object of the present invention is to provide a simplified process and a device suitable for carrying out same, which makes possible the reliable measurement of flow parameters without an enlargement of the dead space, requires little space and affects the flow resistance only insignificantly and guarantees sufficient accuracy at low costs.

The present invention comprises an acoustic process, in which the gas flow itself excites a source of sound and thus ensures the sending of an evaluable acoustic signal.

The present invention comprises a process for measuring flow parameters in flowing gases, comprising at least the following steps:
arrangement of a means for flow-induced sound generation in the area of the flow to be measured;
measurement of the frequency and/or the level of the sound generated as acoustic parameters; and
determination of the flow parameters to be measured by processing the measured acoustic parameters.

It is irrelevant in this connection whether the means for flow-induced sound generation is placed directly and briefly for the purposes of measurement only or whether it is placed by integration in components intended for flowthrough. Flow-induced sound generation in the sense of the present invention is defined as sound generation that is carried out by the flowing gases exciting a source of sound in the area of the flow to be measured and thereby bringing about the generation of sound, which leads to the presence of a sufficiently informative acoustic measured signal. This measured signal is received by suitable means and processed by an evaluating unit such that pertinent information can be obtained for characterizing the flow to be measured. It is especially advantageous if the flow-induced sound generation takes place predominantly at a frequency that unambiguously depends on the direction of flow, the frequency of the emitted sound is measured and the direction of flow of the flowing gas is determined from the measured frequency. This advantageous embodiment is advantageous especially if statements are to be made on the balance from the volume flow and the direction of flow.

Furthermore, it is advantageous if the flow-induced sound generation takes place in such a way that the level of the sound generated depends in an unambiguous manner on the velocity of flow at least in an evaluable frequency range, the sound level is measured in at least part of this frequency range, and the velocity of flow of the flowing gas is determined from the measured sound level. The kind of the unambiguous dependence between the sound level and the velocity of flow can be predicted by corresponding modelings or obtained by calibrations or calibrating measurements.

Furthermore, it may be advantageous if the flow-induced sound generation takes place in such a way that the frequency of the sound generated depends in an unambiguous manner on the velocity of flow at least in an evaluable frequency range, the frequency of the sound generated is measured and the velocity of the flowing gas is determined from the measured sound frequency. The kind of the unambiguous dependence between the frequency of the generated sound and the velocity of flow can likewise be predicted by corresponding modelings or obtained by calibrations or calibrating measurements.

It was found that the process according to the present invention can be used especially advantageously to obtain measured parameters that are to be used to characterize the breathing gas flows during the respiration of a patient. An essential advantage of the process according to the present invention is that no direct connection needs to be established between the site at which the measured signal is generated and the evaluating unit. It is rather sufficient to place an acoustic signal pick-up in the vicinity of the signal generation, which can mean decisive advantages in terms of handling, especially in clinical practice.

The process according to the present invention is carried out with a device that makes possible the measurement of flow parameters in flowing gases and comprises at least one means for flow-induced sound generation as well as at least one means for measuring the sound generated. The means for flow-induced sound generation is arranged in the area of the flow to be measured. Especially reliable measured values, which make it possible to obtain accurate information on the flow to be measured by an accurate extrapolation, are obtained if the means for flow-induced sound generation is integrated in a closed flow path. This happens, for example, when the means for flow-induced sound generation is integrated in the path of routing the gas of a respirator. It is especially advantageous if the means for flow-induced sound generation is designed such that it emits sound waves whose frequency depends on the direction of flow. Furthermore, it is advantageous if the means for flow-induced sound generation is designed such that it emits sound waves whose amplitude depends in an unambiguous manner on the velocity of flow at least in an evaluable frequency range. These requirements can be met, for example, by the means for flow-induced sound generation comprising a hollow structure acting as a flute. The hollow structure acting as a flute occupies part of the cross section of the flow path, in which the flow to be measured takes place. A wall of the hollow structure has differently directed notches of different sizes, at which the arriving flow generates sound. Due to the different directions of the notches, the flows arrives, depending on the direction of flow, at least at one notch such that no appreciable noise will be generated, whereas an acoustic signal with a defined frequency is generated at the other notch. If the direction of flow reverses, an acoustic signal is generated due to the different direction at the notch at which the flow previously arrived without generating appreciable noise. Due to the different dimensioning of the notches, this signal has a different frequency. The particular prevailing velocity of flow can be inferred from the loudness of the particular acoustic signal released. Consequently, the notches make possible a sound emission that depends on the direction of flow and the velocity of flow.

According to another advantageous embodiment of a device for carrying out the process according to the present invention, the means for flow-induced sound generation comprises elastically deflectable reeds. These may likewise be arranged such that individual reeds are deflected, depending on the direction of flow, while others are flown past essentially with little noise. If these reeds have different resonant frequencies, an acoustic signal that depends on the direction of flow and the velocity of flow is likewise generated. The principle is similar to that of sound generation by an arrangement of reeds in a mouth-organ.

In another advantageous embodiment, the device for measuring flow parameters according to the present invention has a means for flow-induced sound generation, which comprises at least one component which is to be set into rotation by the flowing gas and whose speed depends on the velocity of flow in an unambiguous manner. The rotating component is designed such that the rotation itself leads to the emission of an acoustic signal, from which the velocity of flow can be inferred. It is especially advantageous if it has, moreover, means for recognizing the direction of rotation of the component to be set into rotation by the flowing gas. As a result, the velocity of flow and the direction of flow can again be inferred and corresponding measured signals can be sent for processing.

Such a device makes it possible to carry out the flow-induced generation of sound, whose frequency makes it possible to obtain unambiguous information on the direction of flow and the velocity of flow. This is especially advantageous if an accurate level measurement is difficult due to the development of interfering noises.

Another advantageous embodiment of the device for flow measurement according to the present invention is characterized in that the means for flow-induced sound generation comprises at least one deformable component, which is provided with openings contributing to the sound generation and which assumes different positions as a function of the direction of flow, and different sound frequencies are emitted due to the different directions of the openings contributing to the sound generation. The velocity of flow and the direction of flow can in turn be inferred from the amplitude and the frequency of the acoustic measured signals. It is especially advantageous if the means for flow-induced sound generation is designed for sound generation in the ultrasound range. An especially low load due to interfering noises can be achieved as a result in clinical practice.

Various sensors are conceivable for detecting the emitted acoustic measured signals, and various types of microphones are clearly to be given preference. In case of a corresponding sensitivity of the measurement method according to the present invention, it is possible to achieve distances between the source of sound and the microphone that make comfortable handling possible during the use of the measurement process according to the present invention. The need to lay supply lines in the vicinity of the breathing gas line is eliminated altogether. Due to the miniaturization of the means for flow-induced sound generation, the flow resistance is not affected appreciably. Furthermore, the means for flow-induced sound generation can be integrated in the components that are present in case of a usual breathing gas supply anyway, i.e., for example, in a Y-piece, in a tube or a so-called endotracheal catheter or in adapter pieces used otherwise for measurement purposes in the vicinity of the tube or the Y-piece. As a result, it is not necessary to take measures that would lead to an enlargement of the dead space for the measurement process according to the present invention. The robust design of certain means for flow-induced sound generation, i.e., for example, miniaturized flute or reed arrangements, leads to low sensitivity to particles being entrained in the flow, on the one hand, and to availability at a low cost. As a result, it is possible to carry out the process according to the present invention at least partially with disposable articles. In particular, the means for flow-induced sound generation can be used as disposable articles.

The present invention will be explained in greater detail on the basis of exemplary embodiments. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
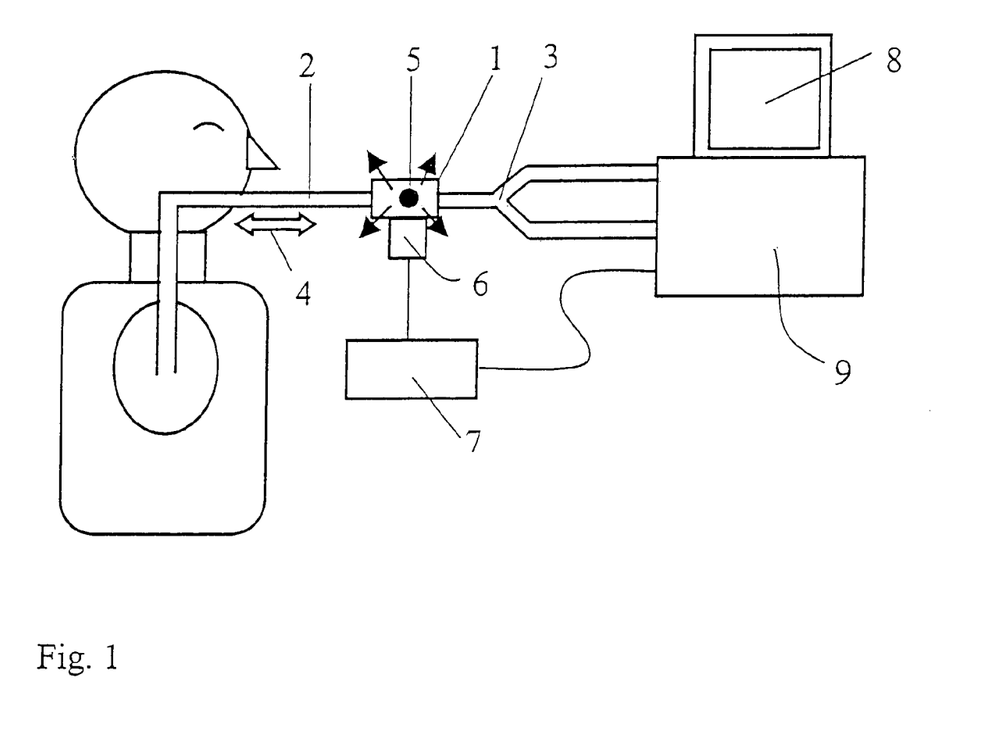
FIG. 1 is a schematic arrangement for carrying out the process according to the present invention.

Referring to the drawings in particular, FIG. 1 shows a schematic arrangement for carrying out the process according to the present invention during the respiration of a patient. A flow sensor housing 1 is arranged between a tube 2 and a Y-piece 3. Flow with cyclic reversal of direction takes place up to the branching of the Y-piece 3. A source of sound 5 operated passively by respiration air is located in the flow sensor housing 1. During the respiration cycle, this source of sound generates acoustic signals, which can be received by a microphone probe 6, which is located outside the flow sensor housing 1. The source of sound 5 is constructed such that it generates a different acoustic frequency during inspiration than during expiration. The velocity and the volume flow that is flowing through the tube 2 can be determined from the spectrum of the acoustic signals, by means of a device for digital signal processing 7, and the velocity of flow can be inferred from the loudness, measured in dB, and/or the direction of the volume flow can be inferred from different tone pitches, measured in Hertz. The flow parameters determined can be displayed on a monitor 8 and used to control the respirator 9.

Figure 2:
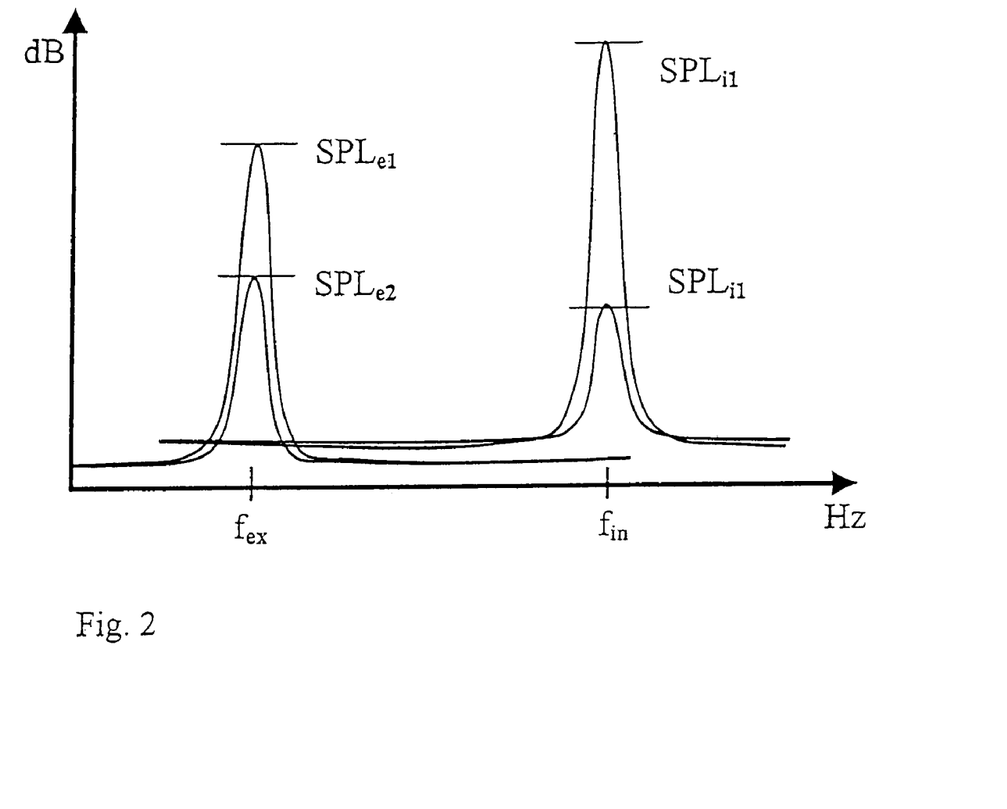
FIG. 2 is an exemplary spectrum of the acoustic measured signals.

FIG. 2 shows the qualitative curve of an exemplary spectrum of the acoustic measured signals at different intensities of respiration by the patient. The sound pressure level (SPL) is measured. Two local maxima $f_{ex}$, $f_{in}$ are clearly visible, and the frequency of a maximum can be assigned to a direction of flow and the level at the maximum corresponds to a velocity of flow that is to be assigned to this level. In case of respiration with tidal volumes set at relatively high levels, a level of $SPL_{e1}$ can be measured during expiration at the frequency $f_{ex}$ characteristic of the expiration and a level of $SPL_{i1}$ can be measured during inspiration at the frequency $f_{in}$ characteristic of the inspiration.

By contrast, only a level of $SPL_{e2}$ can be measured during expiration at the frequency $f_{ex}$ characteristic of the expiration and a level of $SPL_{i2}$ can be measured during inspiration at the frequency $f_{in}$ characteristic of the inspiration in case of respiration with tidal volume flows set at relatively low values. The flow can be unambiguously characterized on the basis of these measured parameters.

Figure 3:
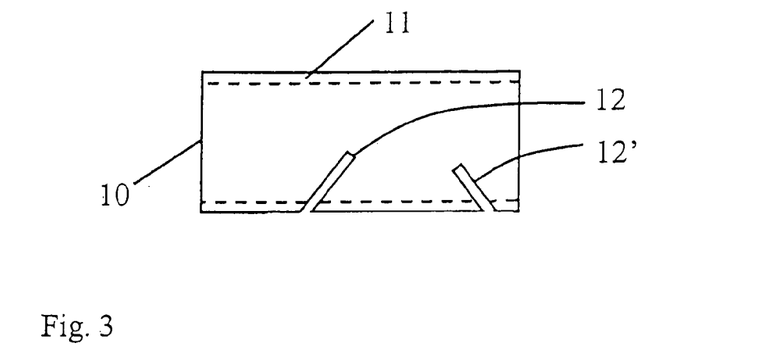
FIG. 3 is a schematic view of a hollow structure according to the present invention acting as a flute.

FIG. 3 shows a schematic view of a hollow structure 10 acting as a flute as a means for flow-induced sound generation. The wall 11 of this hollow structure has two slot-shaped notches 12, 12' of different depths, which are arranged obliquely in relation to one another. The depth of the notches 12, 12' determines the frequency of the particular acoustic signals emitted, whereas the direction of orientation contributes to the selection of the notch contributing to the sound emission in connection with the particular direction of flow. By selectively exciting individual, obliquely positioned notches 12 or 12', it is thus possible to generate an acoustic signal whose frequency depends on the direction of flow and whose intensity depends on the velocity of flow. The example should consequently be understood to be a passive source of sound in the form of a microflute, which generates different tones during inspiration or expiration, and different loudnesses of the tones correspond to different volume flows.

Figure 4:
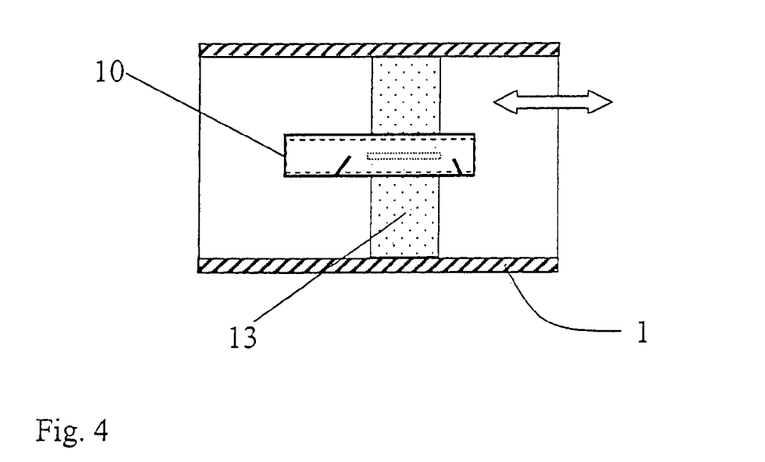
FIG. 4 is a schematic view of the arrangement of a hollow structure according to the present invention in a channel for guiding breathing gas.

FIG. 4 shows how the hollow structure 10 acting as a flute is arranged symmetrically in the direction of flow in the sensor housing 1 by means of a multipart holding system 13. The multipart holding system may consist, for example, of a plate.

Figure 5:
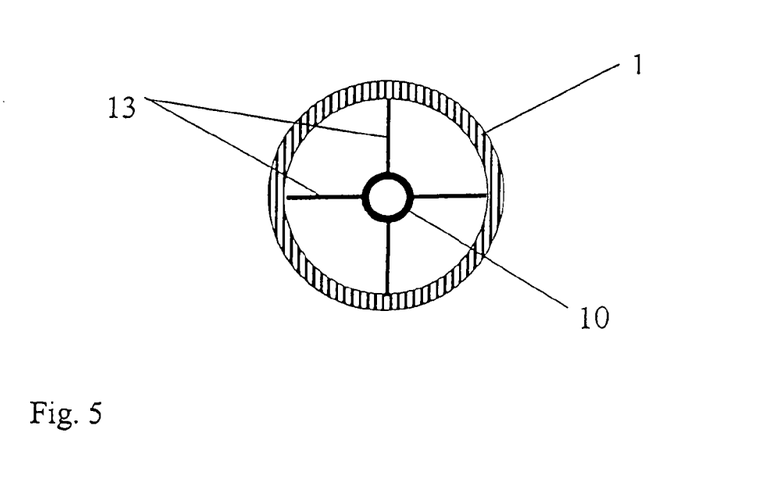
FIG. 5 is an arrangement identical to that in FIG. 4 as a sectional view with a section plane at right angles to the direction of flow.

FIG. 5 shows the same arrangement in the form of a sectional view, the sectional view extending with a plane at right angles to the direction of flow. The hollow structure 10 acting as a flute is arranged in the arrangement in the form of a miniaturized flute along the principal axis symmetrically in the channel for guiding breathing gas, which is formed by the wall of the sensor housing 1. Such a microflute can be shaped such that, similarly to a dog whistle, it generates sound waves in the ultrasound range, as a result of which there is no additional sound load in clinical practice.

As an alternative, an asymmetrical arrangement outside the center of the flow path is possible as well.

Figure 6:
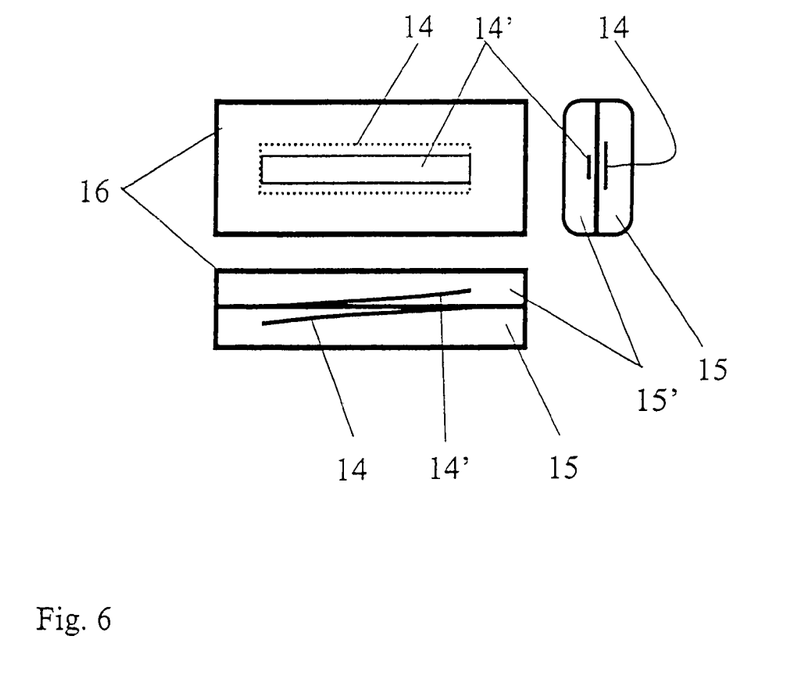
FIG. 6 is a three-sided view of an arrangement for flow-induced sound generation with elastically deflectable reeds.

FIG. 6 shows a three-sided view of an arrangement for flow-induced sound generation with elastically deflectable reeds 14, 14' as another embodiment of the means according to the present invention for flow-induced sound generation.

This arrangement works according to the principle of a mouth-organ, wherein metal strips of different size and thickness, which are excited by the flow to swing and thus generate sound waves, are arranged as a vibrating reed 14, 14', are arranged in two separate channels 15, 15'. The channels 15, 15' are formed by a capsule 16, which ensures the guiding of the flow at least in the vicinity of the area in which the sound is generated.

Figure 7:
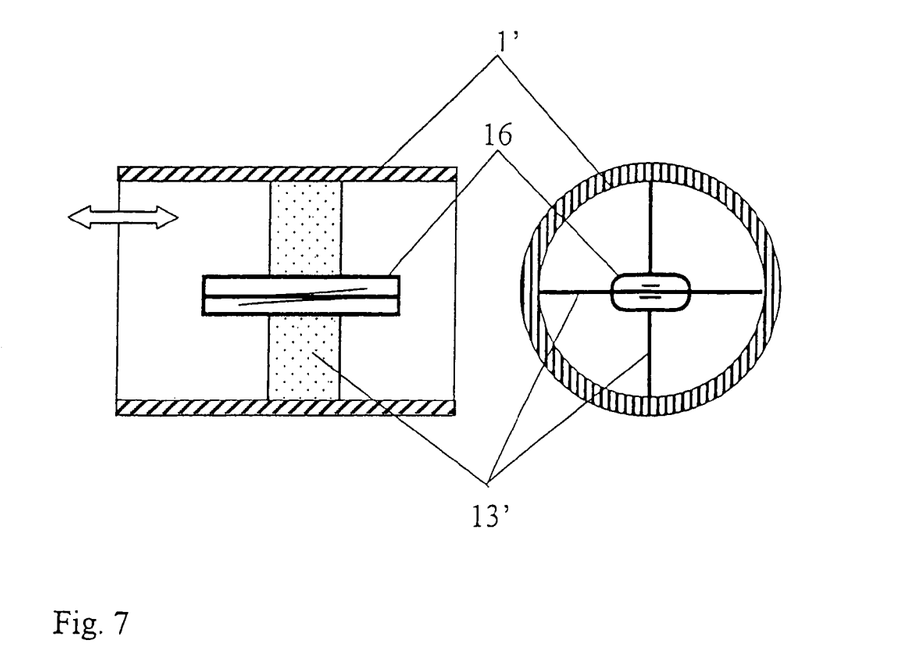
FIG. 7 is a two-sided view of an arrangement with elastically deflectable reeds in a channel for guiding breathing gas.

FIG. 7 illustrates that such an encapsulated reed arrangement can be arranged, analogously to a miniaturized flute, in a channel for guiding the breathing gas, which is formed by the wall of the sensor housing 1'. Fastening is performed by means of a multipart holding system 13'.

Figure 8:
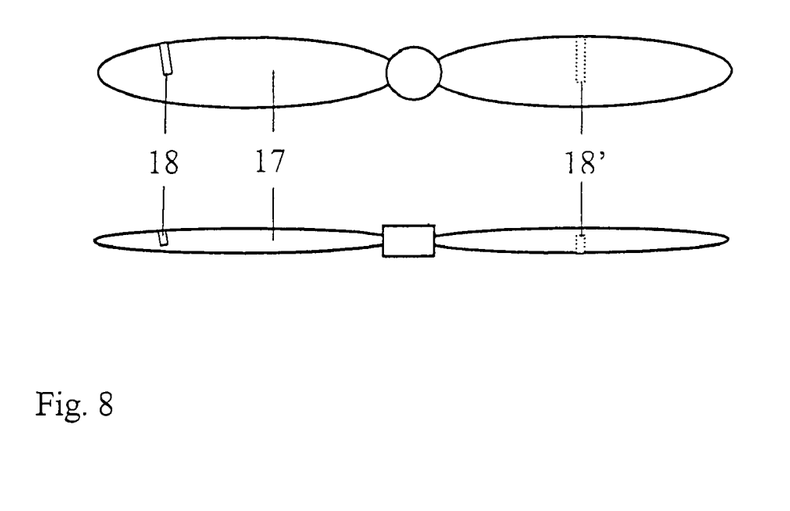
FIG. 8 is a two-sided view of a propeller modified for flow-induced sound generation.

FIG. 8 shows a two-sided view of a two-blade propeller 17 modified for flow-induced sound generation. This propeller is set into rotation by the gas flow to be measured, and the direction of rotation depends on the direction of flow. The propeller 17 is designed such that it has a sufficiently low moment of inertia in order to make possible measurements with alternating directions of rotation, which measurements are resolved for individual breaths. The blades are provided with a blunt-ended notch 18, 18' each. The notches 18, 18' are arranged asymmetrically and in opposite directions and have different dimensions. Due to the arrangement in different directions, an evaluable sound generation always takes place at one notch only in case of rotation. The frequency and the level of the acoustic signal depend on the direction of rotation and the speed of rotation and make it possible to determine the direction of flow and the velocity of flow at the site of arrangement. In a variant of the exemplary embodiment, such a propeller may have various other means for affecting the flow on the flown-past surfaces of the blades, which said means bring about direction- and velocity-dependent sound emissions. These may be, for example, fence or lamellar arrangements.

Figure 9:
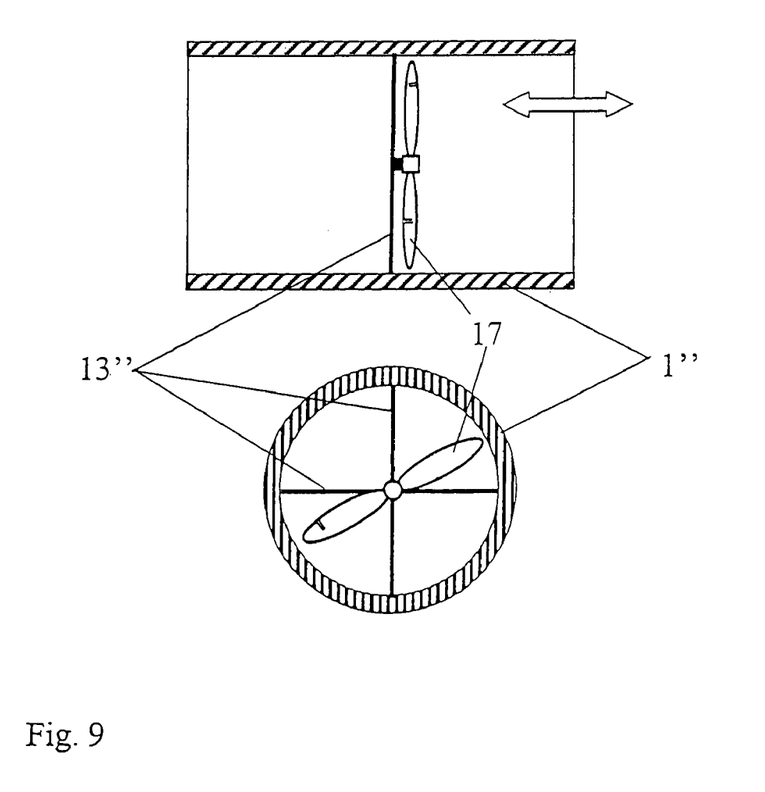
FIG. 9 is a two-sided view of an arrangement with such a propeller in a channel for guiding breathing gas.

FIG. 9 shows the arrangement of a two-blade propeller 17 modified for flow-induced sound generation in a channel for guiding breathing gas, which channel is formed by the wall of the sensor housing 1''. The fastening is performed by means of a multipart holding system 13''.

Figure 10:
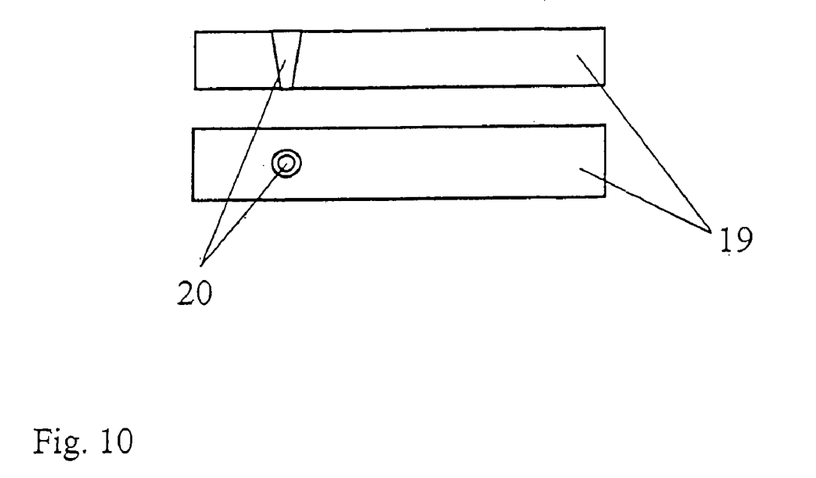
FIG. 10 is a two-sided view of a deformable component designed for flow-induced sound generation.

FIG. 10 shows a two-sided view of a deformable component designed for flow-induced sound generation in the form of a miniaturized transverse beam 19, which is provided with a conical hole 20.

Figure 11:
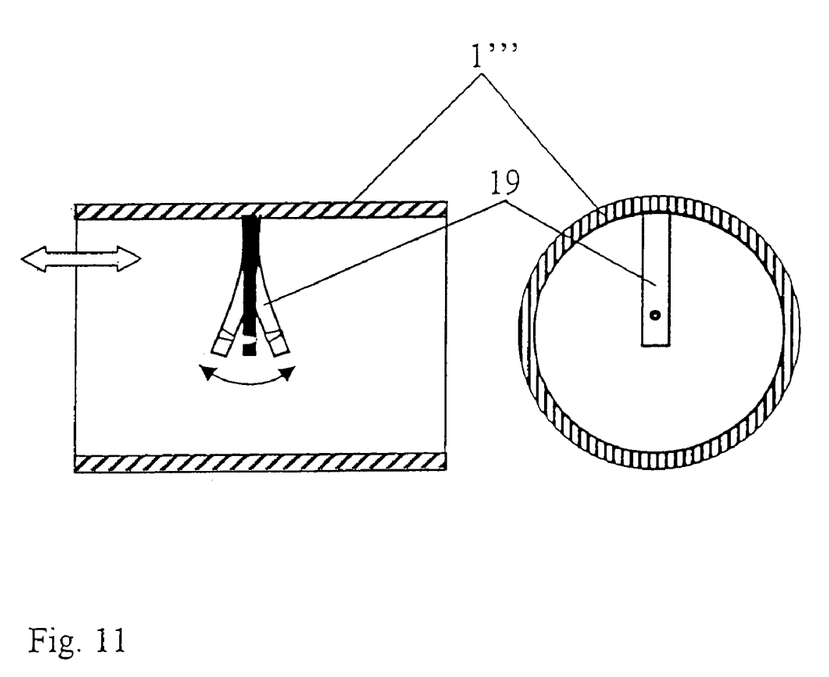
FIG. 11 is a two-sided view of an arrangement with such a component in a channel for guiding breathing gas.

FIG. 11 shows the manner of arrangement of such a transverse beam 19 in a channel for guiding breathing gas, which is formed by the wall of the sensor housing 1'''. The transverse beam 19 is fastened on one side to the wall of the sensor housing 1'''. The axis of the conical hole 20 extends in parallel to the direction of flow in the relaxed state of the transverse beam 19. Due to the different widths of opening of the conical hole 20, acoustic signals of different frequencies are generated as a function of the direction of flow. At the same time, the flow acting on the transverse beam 19 brings about a deformation of the transverse beam 19, the deflection being determined by the velocity of flow. Due to this deflection, the axis of the conical hole 20 is pivoted to different extents in relation to the direction of flow, which likewise affects the frequency of the signal generated. In addition, the velocity of flow affects the level of the signal generated. The direction of flow determines in this arrangement a direction-dependent frequency range, within which a velocity-dependent fine determination is carried out. Information can thus be obtained from the frequency analysis alone concerning the direction of flow and the velocity of flow at the site of the conical hole 20.

To guarantee the generation of sound even at low volume flows, the means for flow-induced sound generation can be installed with means for flow acceleration in a sensor housing or in adjacent components of the overall arrangement. Measures can be taken for this for homogenizing the flow in order to guarantee a higher accuracy of measurement by single-point measurement. The source of sound designed according to the present invention can thus be used in flow sensors with so-called flat measuring sections.

The sensor housing has fitting interfaces to the tube adapter and the Y-piece, respectively, at both ends in this example, However, the source of sound may be directly integrated in the Y-piece and the tube, respectively, in an alternative embodiment.

An arrangement according to the present invention is characterized by a special robustness, especially a more robust construction compared to hot wires or planar measuring elements. The energy consumption will be lower, because the source of sound itself is operated passively. Due to the design, there will be a higher tolerance to water of condensation, sputum and carried particles. Besides the ease of operation and advantages that can be achieved in terms of handling and use, it shall be pointed out that a sensor housing with fitting interfaces or adapters to adjacent components may be designed especially advantageously as a carrier of disposable sensors. Only the microphone or evaluating unit is used in multiple copies in this case, whereas the sound generator proper is discarded after a single use, as a result of which a complicated cleaning and sterilization can be eliminated.

While specific embodiments of the invention have been shown and described in detail to illustrate the application of the principles of the invention, it will be understood that the invention may be embodied otherwise without departing from such principles.

What is claimed is:

1. A process for measuring flow parameters in flowing gas, the process comprising the steps of:
   arranging a means for flow-induced sound generation in an area of a flow to be measured, which said flow generates a frequency from said means for flow-induced sound generation that depends on the direction of said flow;
   measuring said frequency and/or the level of a sound generated as acoustic parameters to provide measured said acoustic parameters; and
   determining the flow parameters by processing the measured said acoustic parameters.

2. A process in accordance with claim 1, wherein the frequency of the emitted sound is measured and the direction of flow of the flowing gas is determined from the measured frequency.

3. A process in accordance with claim 1, wherein the flow-induced sound generation is carried out such that the sound level is measured in at least part of this frequency range and a velocity of flow of the flowing gas is determined from the measured sound level.

4. A process in accordance with claim 1, wherein:
   the flowing gas passes through a flow tube of a respiration system for a patient;
   said means for flow-induced sound generation is disposed in said flow tube in said area of a flow to be measured;
   said step of measuring said frequency and/or the level of a sound generated as acoustic parameters to provide measured said acoustic parameters includes measuring with a measuring device disposed outside of said flow tube; and the measured parameters are used to characterize the breathing gas flows during the respiration of the patient.

5. A device for measuring flow parameters in a flowing gases, the device comprising:
 a sound generating means for flow-induced sound generation in the area of the flow to be measured, which generates and emits sound waves having a frequency that depends on the direction of the flow;
 a device for measuring the frequency of the sound generated as acoustic parameters to provide measured acoustic parameters; and
 a processor determining the flow parameters by processing the measured acoustic parameters including determining flow direction.

6. A device in accordance with claim 5, wherein the sound generating means for flow-induced sound generation emits sound waves whose amplitude depends on the velocity of flow at least in an evaluable frequency range.

7. A device in accordance with claim 5, wherein the sound generating means for flow-induced sound generation comprises a hollow structure having a flute action.

8. A device in accordance with claim 7, wherein said hollow structure has notches, which make possible a sound emission that depends on the direction of flow and the velocity of flow.

9. A device in accordance with claim 5, wherein the sound generating means for flow-induced sound generation comprises elastically deflectable reeds.

10. A device in accordance with claim 5, wherein the sound generating means for flow-induced sound generation comprises at least one component which is to be set into rotation by the flowing gas and whose speed of rotation depends on the velocity of flow.

11. A device in accordance with claim 10, further comprising means to recognize the direction of rotation of the component set into rotation by the flowing gas.

12. A device in accordance with claim 5, wherein the sound generating means for flow-induced sound generation comprises at least one deformable component, which is provided with openings contributing to the sound generation and which assumes different positions as a function of the direction of flow, wherein different sound frequencies are emitted due to the different orientations of the openings contributing to the sound generation.

13. A device in accordance with claim 5, wherein at least one means for flow-induced sound generation is designed for sound generation in the ultrasound range.

14. A device in accordance with claim 5, further comprising: a respiration/ventilation flow tube of a respiration/ventilation system for a patient, the flowing gas passing through said flow tube, said sound generating means being disposed fully in said flow tube in said area of the flow to be measured and said device for measuring acoustic parameters is disposed entirely outside of said flow tube whereby the measured parameters are used to characterize breathing gas flows during the respiration/ventilation of a patient.

15. A flowing fluid flow parameter measuring systems comprising:
 a flow tube with flowing fluid passing through the flow tube in one of two flow directions;
 a flow-induced sound generation device for generating sound in response to the flow of the fluid to be measured said sound generating device being disposed entirely in said flow tube and generating sound having a frequency that depends on the direction of the flowing fluid; and
 a measuring device for measuring the frequency of the sound generated during the flow to be measured as an indication of flow direction of the flowing fluid, the measuring device being disposed entirely outside of said flow tube.

16. A flowing fluid flow parameter measuring system according to claim 15, further comprising:
 a processor for making a determination of the flow parameters to be measured by processing the acoustic parameters measured.

17. A flowing fluid flow parameter measuring system in accordance with claim 16, wherein the flow-induced sound generation takes place predominantly at said frequency or in a frequency range that depends on the direction of flow in an unambiguous manner, and the frequency of the emitted sound is measured by the measuring device and the direction of flow of the flowing gas is determined from the measured frequency by the processor.

18. A flowing fluid flow parameter measuring system in accordance with claim 16, wherein the flow-induced sound generation is carried out in such a way that the sound level of the sound generated unambiguously depends on the velocity of flow and the velocity of flow is determined by the sound level measured.

19. A flowing fluid flow parameter measuring system in accordance with claim 16, wherein the flow-induced sound generation is carried out such that the frequency of the sound generated unambiguously depends on the velocity of flow, and the frequency of the sound is measured, and the velocity of flow of the flowing gas is determined from the measured frequency.

20. A flowing fluid flow parameter measuring system in accordance with claim 16, further comprising respirator components wherein the measured parameters are used to characterize the breathing gas flows during the respiration of a patient.

21. A flowing fluid flow parameter measuring system in accordance with claim 20, wherein a flow-induced sound generation device is integrated in a respirator flow path and the measuring system device is outside the flow path.

* * * * *